United States Patent [19]

Safir et al.

[11] Patent Number: 5,002,603
[45] Date of Patent: Mar. 26, 1991

[54] METHOD AND COMPOSITIONS FOR STIMULATING VESICULAR-ARBUSCULAR MYCORRHIZAL FUNGI

[75] Inventors: Gene R. Safir; Muraleedharan G. Nair; Jose O. Siqueira, all of East Lansing, Mich.

[73] Assignee: Board of Trustees operating Michigan State University, East Lansing, Mich.

[21] Appl. No.: 444,838

[22] Filed: Dec. 4, 1989

[51] Int. Cl.$^5$ .............. A01N 43/16; C07D 311/22
[52] U.S. Cl. ........................................ 71/88; 549/403
[58] Field of Search ...................... 549/403; 71/88

[56] References Cited

U.S. PATENT DOCUMENTS 4,294,037 10/1981 Mosse et al. ........................ 47/59

FOREIGN PATENT DOCUMENTS 0172085 2/1986 European Pat. Off. .
63-8797 3/1988 Japan .

OTHER PUBLICATIONS

Harley, J. L., and Smith, S. E., Mycorrhizal Symbiosis, Academic Press, London, pp. VI, VII and pp. 1-31, Introduction, Chapter 3, 64-103, Chapter 5, 104-116, (1983).
Safir, G. R., Ecophysiology of VA Mycorrhizal Plants, CRC Press, Boca Raton, Chapter 2; pp. 5-25, Chapter 9; 171-192 and Chapter 10; 193-211 (1987).
Powell, G. L. and Bagyaraj, D. J., VA Mycorrhiza, CRC Press, Boca Raton, Chapter 1; pp. 1-3, Chapter 6; pp. 113-130, Chapter 9; pp. 187-203, Chapter 10; pp. 205-223 (1984).
Smith, S. E. and Gianinazzi-Pearson, V., Ann. Rev. Plant Physiol. Plant Mol. Biol., 39:221-244 (1988).
Jeffries, P., Use of Mycorrhizae in Agriculture, Crt. Rev. Biotechnol., 5:319-357 (1987).
Siqueira, J. O. and Franco, A. A., Biotechnologia do solo, MEC/ABEAS, Brasilia, Chapter 5, pp. 125-177 (1988).
Hepper, C. M., VAM Spore Germination and Hyphal Growth in vitro: Prospects for Axenic Culture, In:

Proc. 7th NACOM, Sylvia et al. (ed), University of Florida, Gainesville, 172-174 (1987).
Mosse, B., Some Studies Relating to "Independent" Growth of Vesicular-Arbuscular Endophytes, Can. J. Bot. 66:2533-2540 (1988).
Siqueira, J. O. et al., Can J. Microbiol. 31:965-972 (1985).
Becard, G. and Fortin, J. A., New Phytol. 108:211-218 (1988).
Mosse, B. and Hepper, C. M., Physiol. Plant Pathol. 5:215-223 (1975).
Siqueira, J. O., Cultura Axenica e Monoxenica dos Fungos Micorizicos Vesiculo-Arbusculares. In: Proc. II Reuniao Bras. Micorrizas, Sao Paulo, Sec. Meio Ambiente. pp. 44-70 (1987).
Elias, K. S. and Safir, G. R., Appl. Environ. Microbiol. 53:1928-1933 (1987).
Glenn, M. G. et al., New Phytol. 110:217-225 (1988).
Bonfate-Fasolo in Scannerini et al., in Gianinazzi-Pear- (List continued on next page.)

Primary Examiner—Richard L. Raymond
Assistant Examiner—S. Mark Clardy
Attorney, Agent, or Firm—Ian C. McLeod

[57] ABSTRACT

A method and compositions for stimulating the growth of vesicular-arbuscular mycorrhizal fungi alone or in the presence of a plant material using isoflavonoid compounds is described. The isoflavonoids are preferably of the formula:

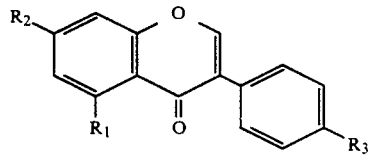

wherein $R_1$, $R_2$ and $R_3$ are selected from the group consisting of hydrogen, hydroxyl and alkoxy, particularly methoxy.

12 Claims, 10 Drawing Sheets

OTHER PUBLICATIONS son, V. eds., Cell to Cell Signals In Plant, Animal and Microbial Symbiosis. Springer Verlag, Berlin, pp. 219–235 (1988).

Rolfe and Gresshoff, Ann. Rev. Pl. Physiol. Pl. Mol. Biol. 39: 297–319 (1988).

Kapulnik, Y. et al., Plant Physiol. 84:1193–1196 (1987).

Steffens, J. C. et al. Ann. Bol. 50:1–7 (1982).

Bailey, J. A., ed., Biology and Molecular Biology of Plant-Pathogen Interactions, Springer Verlag, Berlin, pp. 29–36 (1986).

Palacios, R. and Verma, D. P. S., ed., Molecular Genetics of Plant-Microbe Interactions, APS, St. Paul, p. 401 (1988).

Templeton, M. D. and Lamb, D. J., Plant, Cell Environ. 11:395–401 (1988).

VanEtten, H. D., Phytochemistry 15:655–659 (1976).

Jacobs, M. and Rubbery, P. H., Science 241:346–349 (1987).

Morandi, D. et al., Physiol. Plant Pathol. 24:357–364 (1984).

Conn, E. E., ed., Opportunities for Phytochemistry in Plant Biotechnology, Plenum Press, New York, Chapter 5; pp. 83–97, Chapter 6, pp. 99–119, Chapter 8; pp. 613–175 (1988).

Powell, G. K. et al., Mol Plant–Microbe Interactions, 1:235–242 (1988).

Scannerini, S. et al., Cell to Cell Signals in Plant, Animal and Microbial Symbiosis, Springer Verlag, Berlin, pp. 73–83, 167–205 (1988).

Wacker, T. L. et al., J. Chem. Ecol. (in press) (1989).

Burggraaf, A. J. P. and Beringer, J. E., New Phytol. 111:25–33 (1989).

Hoch, H. C. and Staples, R. C., Ann. Rev. Phytopathol. 25:231–247 (1987).

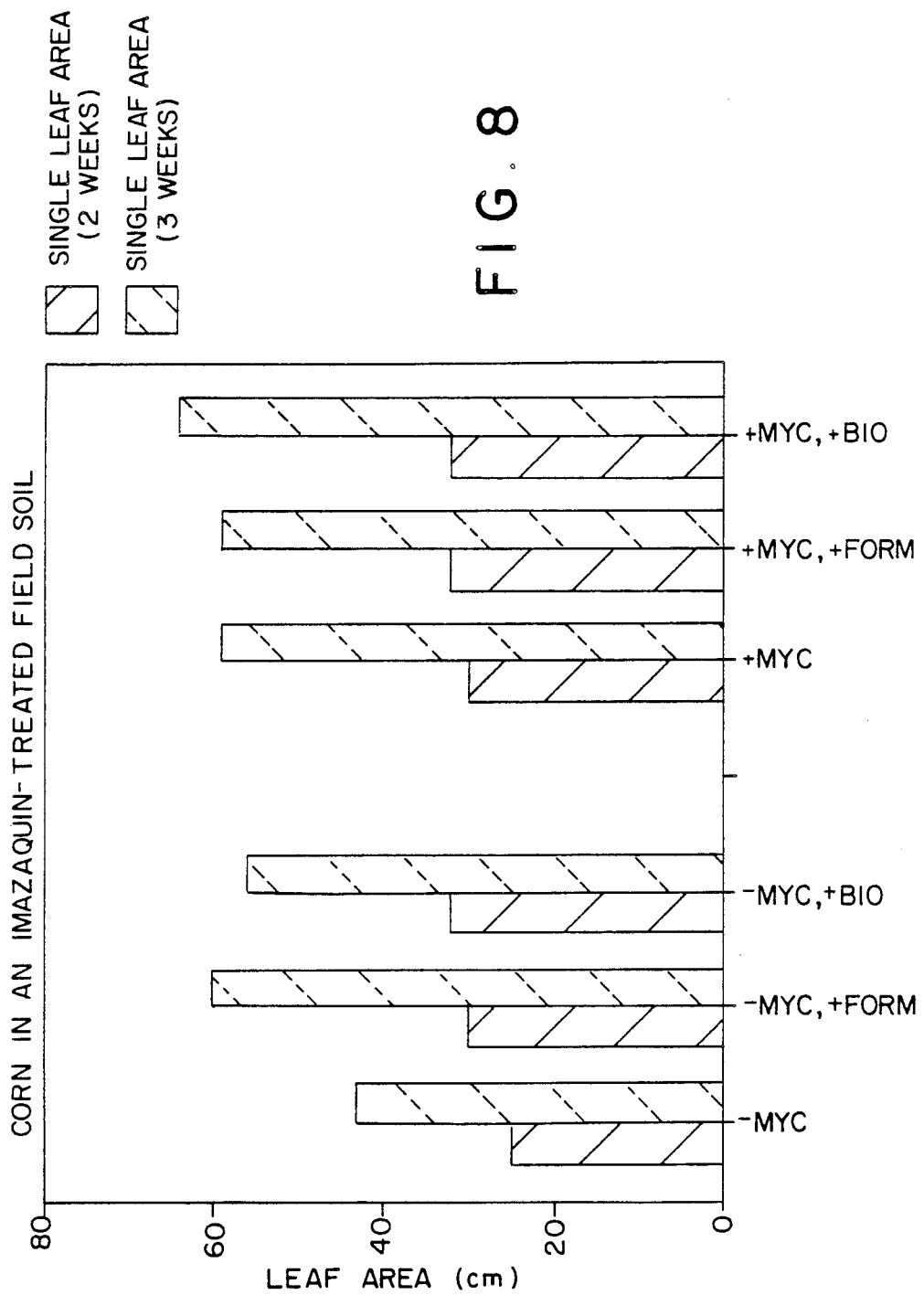

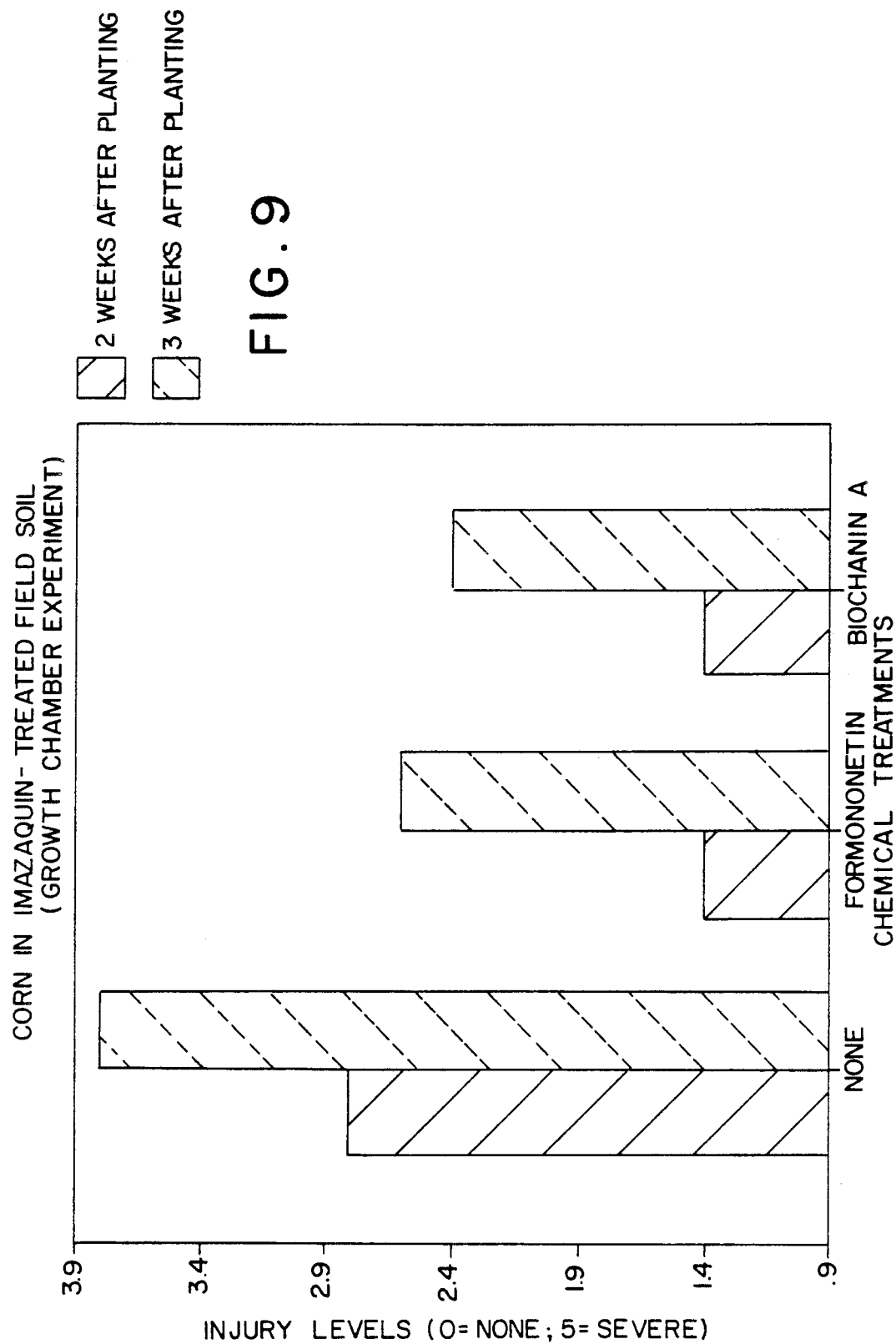

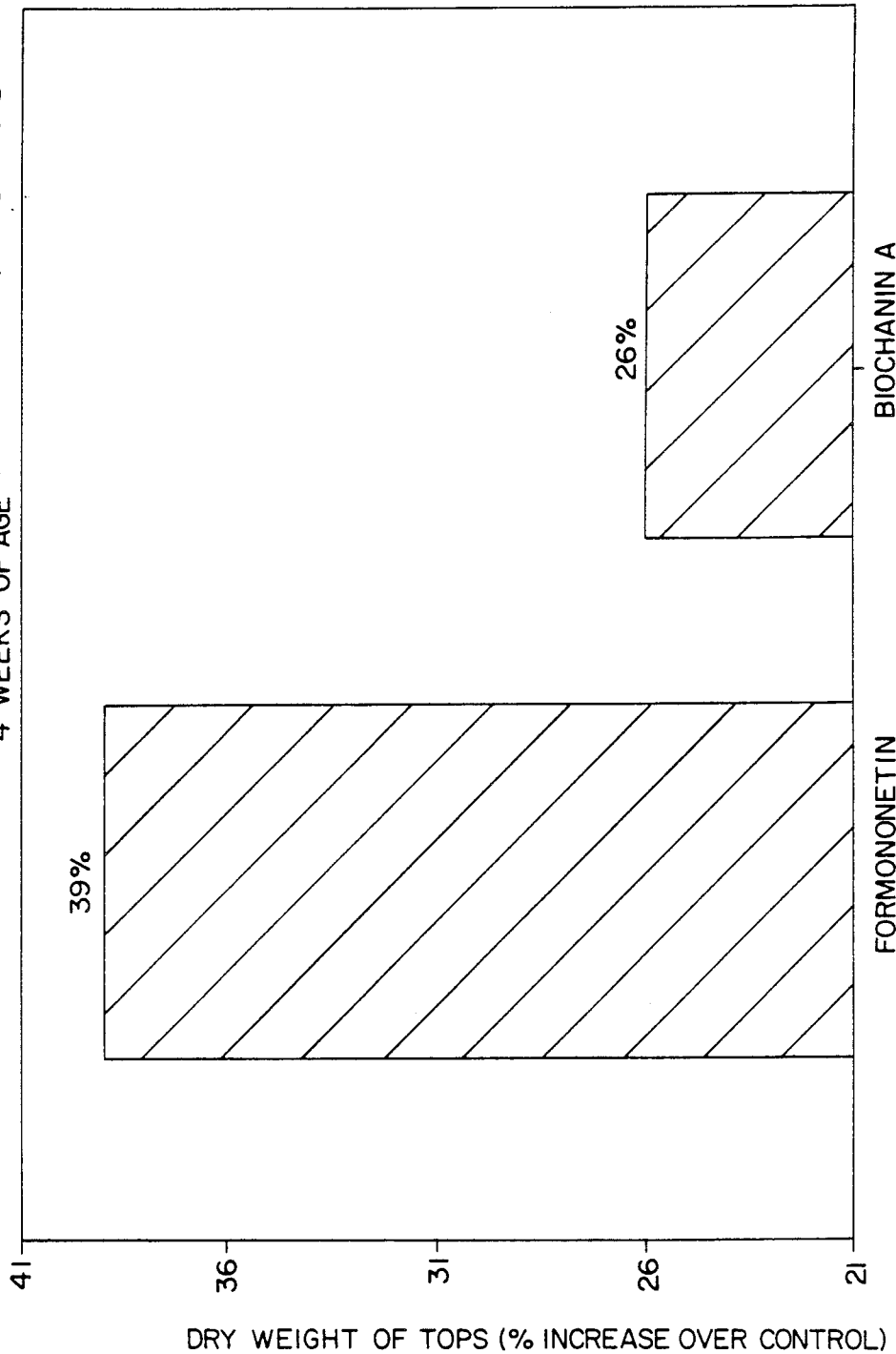

METHOD AND COMPOSITIONS FOR STIMULATING VESICULAR-ARBUSCULAR MYCORRHIZAL FUNGI

BACKGROUND OF THE INVENTION (1) Field of the Invention

The present invention relates to the use of isoflavonoids for the stimulation of vesicular-arbuscular mycorrhizal fungi (VAM) Fungi. In particular, the present invention relates to methods and compositions which use the isoflavonoids to stimulate the growth of plant materials in the presence of the VAM fungi.

(2) Prior Art

Several fungal species which are members of the family Endogonaceae (Zigomycetes) form endophytic symbiotic associations with roots of a large number of vascular plants in virtually all types of terrestrial habitats (Harley, J. L., and Smith, S. E., Mycorrhizal symbiosis. Academic Press, London, p. 483 (1983); Safir, G. R., Ecophysiology of VA mycorrhizal plants. CRC Press, Boca Raton. p. 224 (1987)). These associations are termed vesicular-arbuscular mycorrhizae (VAM) and are known to occur in at least 300,000 plant species, including most agriculturally important crops, with the exception of crucifers and a few other species. As widely known, the VAM fungi can have profound beneficial effects on plant growth, nutrition and tolerance to both abiotic and biotic stress (Powell, G. L. and Bagyaraj, D. J., VA mycorrhiza. CRC Press, Boca Raton. p. 234 (1984); Safir, G. R., Ecophysiology of VA mycorrhizal plants. CRC Press, Boca Raton. p. 224 (1987)). These benefits result from increased soil nutrient uptake, increased nodulation and biological nitrogen fixation in legumes, favored plant-water relationships, reduced disease severity, increased accumulation of plant growth promoting substances and other physiological effects (Smith, S. E. and Gianinazzi-Pearson, V., Ann. Rev. Plant Physiol. Plant Mol. Biol. 39:221-244 (1988)). Reseachers and commercial firms from all over the world have recognized the great biotechnological potential for large scale application of these fungi in agriculture and forestry (Jeffries, P., Use of mycorrhizae in agriculture. Crit. Rev. Biotechnol. 5:319-357 (1987); Powell, C. L. and Bagyaraj, D. J. ed. VA mycorrhiza. CRC Press, Boca Raton. p. 234 (1984); Safir, G. R., ed., Ecophysiology of VA mycorrhizal plants. CRC Press, Boca Raton., p. 224 (1987); and Siqueira, J. 0. and Franco, A. A., Biotechnologia do solo. MEC/ABEAS, Brasilia, p234 (1988)). The use of these fungi as plant or soil inoculants could have significant impacts on agriculture and global environmental quality by reducing fertilizer and pesticide use, by reducing crop loss due to abiotic (metal toxicity, drought, adverse temperature) and biotic (nematodes and pathogens attack) stresses. In addition, these fungi have been shown to improve the survival and early growth of out plantings and increase productivity or re-vegetation in poor and disturbed sites. In fact, the outgrowth of some transplanted forest and fruit species as well as coffee seedlings is known to be improved by a range of 50 to 8000% by proper VAM inoculation. For horticultural and arable crops the reported yield increases have ranged from 5 to 290% by VAM inoculation (Powell, C. L., and Bagyaraj, D. J., ed. VA mycorrhiza. CRC Press, Boca Raton. p234 (1984); Siqueira, J. 0. and Franco, A. A., Biotecnologia do solo. MEC/ABEAS, Brasilia. p235 (1988)).

Considering the concerns with environmental quality in the developed nations; the high fertilizer requirement of tropical soils, where agricultural expansion is expected to happen; and the fact that global phosphate deposits will potentially be exhausted in about 70 years; there is a tremendous worldwide market for VAM inoculum.

The importance of VAM fungi for plant growth in most soils has been accepted and acknowledged by soil chemists, agronomists, horticulturists, ecologists, farmers and nurseryman (Powell, C. L., and Bagyaraj, D. J., ed. VA mycorrhiza. CRC Press, Boca Raton. p234 (1984); Safir, G. R., ed., Ecophysiology of VA mycorrhizal plants. CRC Press, Boca Raton, p224 (1987)), but current inability to supply large quantities of active and effective inoculant represents the main drawback to their large scale use.

The VAM fungi are regarded as obligate biotrophs in that they have not been successfully cultivated under axenic conditions (Hepper, C. M., VAM spore germination and hyphal growth in vitro: prospects for axenic culture. In: Proc. 7th NACOM, Sylvia et al. (ed). University of Florida, Gainesville. 172-174 (1987)); Mosse, B. Some studies relating to "independent" growth of vesicular-arbuscular endophytes. Can. J. Bot. 66:2533-2540 (1988); Siqueira, et al Can. J. Microbiol. 31:965-972 ((1985)). The lack of infective VAM fungi makes intensive studies on the basic biology, ecology, host-relationship and inoculant production technology very difficult. The culture of VAM fungi in vitro has frequently been attempted, but has met with variable results (Hepper, C. M., VAM spore germination and hyphal growth in vitro: prospects for axenic culture. In: Proc. 7th NACOM, Sylvia et al. (ed). University of Florida, Gainesville p.172-174 (1987)); Siqueira, et al. Mycologia 74:952-959 (1982); Siqueira, J. 0., et al., Can. J. Microbiol. 31:965-972 (1985)). European patent application No. EP0172085 describes the axenic growth of VAM fungi; however, the growth factors are from a non-plant source and the VAM fungi would have limited ability to infect the plants. Viable spores of most species are readily germinated when plated on suitable media, but germination synchrony and the rate of germ tube growth in the absence of living roots are affected by several innate environmental and nutritional factors (Hepper, C. M., VAM spore germination and hyphal growth in vitro: prospects for axenic culture. In: Proc. 7th NACOM, Sylvia et al. (ed). University of Florida, Gainesville p. 172-174 (1987); Siqueira, J. 0. et al. Can. J. Microbiol. 31:965-972 (1985)). Although spores of most species have no specific nutritional requirement for either germination or hyphal growth, addition of certain factors has been shown to be beneficial, but only to a very limited extent (Siqueira, J. O., Can. J. Mirobiol. 31:965-972 (1985)). Continued hyphal growth and sporulation are only achieved in the presence of living plant roots (Bécard, G. and Fortin, J. A., New Phytol. 108:211-218 (1988); Mosse, B., Can. J. Bot. 66:2533-2540 (1988)). Japanese Patent 63-87973 (1988) showing VAM fungi inoculated with potatoes and various growth accelerators and U.S. Pat. No. 4,294,037 to Mosse et al describes the growth of VAM fungi in the presence of plant roots.

For a long time root exudates have been thought to play an important role in the initiation and extent of VAM formation (Harley, J. 0., and Smith, S.E., Mycorrhizal symbiosis. Academic Press, London. p.483 (1983)). The presence of roots stimulates hyphal growth, even without physical contact (Bécard, G. and Fortin, J. A., New Phytol. 108:211-218 (1988); Mosse, B. and Hepper, C. M., Physiol. Plant Pathol. 5:215-223 (1975); and Mosse, B., Can. J. Bot. 66:2533-2540 (1988)). However, the effects of either root exudates or extracts on spore germination or hyphal growth in vitro are very inconsistent (Harley, J. L. and Smith, S.E., Mycorrhizal symbiosis. Academic Press, London. p.483 (1983); Siqueira, J. 0., Cultura axenica e monoxenica dos fungos micorizicos vesiculo-arbusculares. In: Proc. II Reuniao bras. micorrizas, Sao Paulo, Sec. Meio Ambiente. p.44-70 (1987)). A recent study however, indicated that the quality rather than the quantity of root exudates is an important factor for VAM fungal growth in vitro (Elias, K.S. and Safir, G. R., Appl. Environ. Microbiol. 53:1928-1933 (1987)). The authors suggested the presence of a transient VAM growth factor in the root exudates of phosphorus deprived clover plants.

Non-VAM species such as Brassica appear not to be colonized because they lack a diffusible growth stimulant present near the roots of compatible hosts (Glenn, M. G., et al., New Phytol. 110:217-225 (1988). This agrees with the suggestion that chemical signaling must take place in the early events of VAM establishment (Elias, K. S., and Safir, G. R., Appl. Environ. Microbiol. 53:1928-1933 (1987); Bécard, G. and Fortin, J. A., New Phytol. 108:211-218 (1988); Bonfate-Fasolo in Scannerini et al. (Scannerini, S., Smith, D., Bonfante-Fasolo, P. in Gianinazzi-Pearson, V. eds., Cell to cell signals in plant, animal and microbial symbiosis. Spring Verlag, Berlin. p.414 (1988)).

Low molecular weight phenolic compounds are known to play important roles in a wide variety of plant-microbe systems. In the plant-Rhizobium symbiosis, flavonoids present in root exudates act in a regulatory fashion as inducers or repressors of nod genes on the symbiotic plasmids of the bacteria (Rolfe and Gresshoff, Ann. Rev. Pl. Physiol. Pl. Mol. Biol. 39:297-319 (1988). For instance, luteolin, which induces nod ABC gene expression in R. melliloti, may occur in low concentrations in the alfalfa rhizosphere and limit nodulation and nitrogen fixation (Kapulnik, Y, et al., Plant Physiol. 84:1193-1196 (1987)). Flavonoids may also induce haustorial formation in parasitic plants (Steffens, J. C., et al. Ann. Bot. 50:1-7 (1982)); control plant microbial invasion (Bailey, J. A., ed. biology and molecular biology of plant-pathogen interactions. Spring Verlag, Berlin. p. 415 (1986); Palacios, R. and Verma, D.P.S., ed. Molecular genetics of plant-microbe interactions. APS, St. Paul. p.401 (1988); Templeton, M.D. and Lamb, D. J., Plant, Cell Environ. 11:395-401 (1988); VanEtten, H.D., Phytochemistry 15:655-659 (1976)); act as natural auxin regulators (Jacobs, M. and Rubery, P.H., Science 241:346-349 (1987)) and are known to accumulate as a response to pathogen invasion (Templeton, M.D. and Lamb, C.J., Plant, Cell Environ. 11:395-401 (1988)). Other low molecular weight phenolic compounds can induce gene expression of cytokinin biosynthesis and vir genes in pathogenic Agrobacterium (Conn, E. E., ed. Opportunities for phytochemistry in plant biotechnology. Plenum Press, New York, p.210 (1988)); Powell, G. K., et al., Mol. Plant-Microbe Interactions. 1:235-242 (1988)); regulate cyclic processes in lichens (Scannerini, S., et al., Cell to cell signals in plant, animal and microbial symbiosis. Spring Verlag, Berlin. p.414 (1988)). They can also act as allelopathic compounds and affect both VAM hyphal growth in vitro and root colonization (Wacker, T. L., et al., J. Chem. Ecol. (in press) (1989)).

The VAM fungi are obligate biotrophs. They may have lost the genetic capability for saprophytic growth (or have a depressed part of the required genome) during their long co-evolution with plants (Siqueira, J. 0., Cultura axenica e monoxenica dos fungos micorizicos vesiculo-arbusculares. In: Proc. II Reuniao bras. micorizas, Sao Paulo, Sec. Meio Ambiente. p. 44-70 (1987)), thus permitting the host plant to have complete control of the fungal life cycle through interference with the replication of fungal nuclear DNA as recently suggested (Burggraaf, A.J.P. and Beringer, J.E., New Phytol. 111:25-33 (1989)). In fact, the germination process is readily triggered after spore inbibition (Siqueira et al., Can. J. Microbiol. 31:965-972 (1985)), but at least for one species, nuclear DNA synthesis has not been found during in vitro development (Burggraaf, A.J.P. and Beringer, J.E., New Phytol. 111:25-33 (1989)). Additionally, neither appresoria nor arbuscules (haustorium-like structures) have reported to form in the absence of living roots. It seems that both continued hyphal growth and differentiation are under host control. As observed for other obligate biotrophic fungi (Hoch, H.C. and Staples, R.C., Ann. Rev. Phytopathol. 25:231-247 (1987)) plant messengers or inducers may be needed as triggers for the invaders early growth, development and differentiation.

OBJECTS

It is therefore an object of the present invention to provide a method for producing plant infective VAM fungi in culture or in soil or other planting material. It is further an object of the present invention to provide novel compositions including VAM fungi. Further still, it is an object of the present invention to provide a method and compositions for stimulating plant growth or plant cell growth in the presence of VAM fungi. Further still, it is an object of the present invention to provide a method for improving plant productivity in soils that have phytotoxic levels of herbicides and other pesticides by stimulating the infective VAM fungi. Further still, it is an object of the present invention to provide a method which is simple and economical to use and is formulated in inexpensive agricultural compositions. These and other objects will become increasingly apparent by reference to the following description and the drawings.

IN THE DRAWINGS

FIG. 8 shows the increased leaf area of corn grown in unsterilized field soil in the presence of formononetin and biochanin A. The field soil contains the herbicide imazaquin at levels toxic to corn.

FIG. 9 shows the reduction of herbicide injury to corn in the presence of added formononetin and biochanin A. The injury levels are for the corn plants described in FIG. 8.

FIG. 10 shows the increased dry weight of tops of the corn plants described in FIG. 8 at four (4) weeks of age in the presence of formononetin and biochanin A.

GENERAL DESCRIPTION

Figure 1:
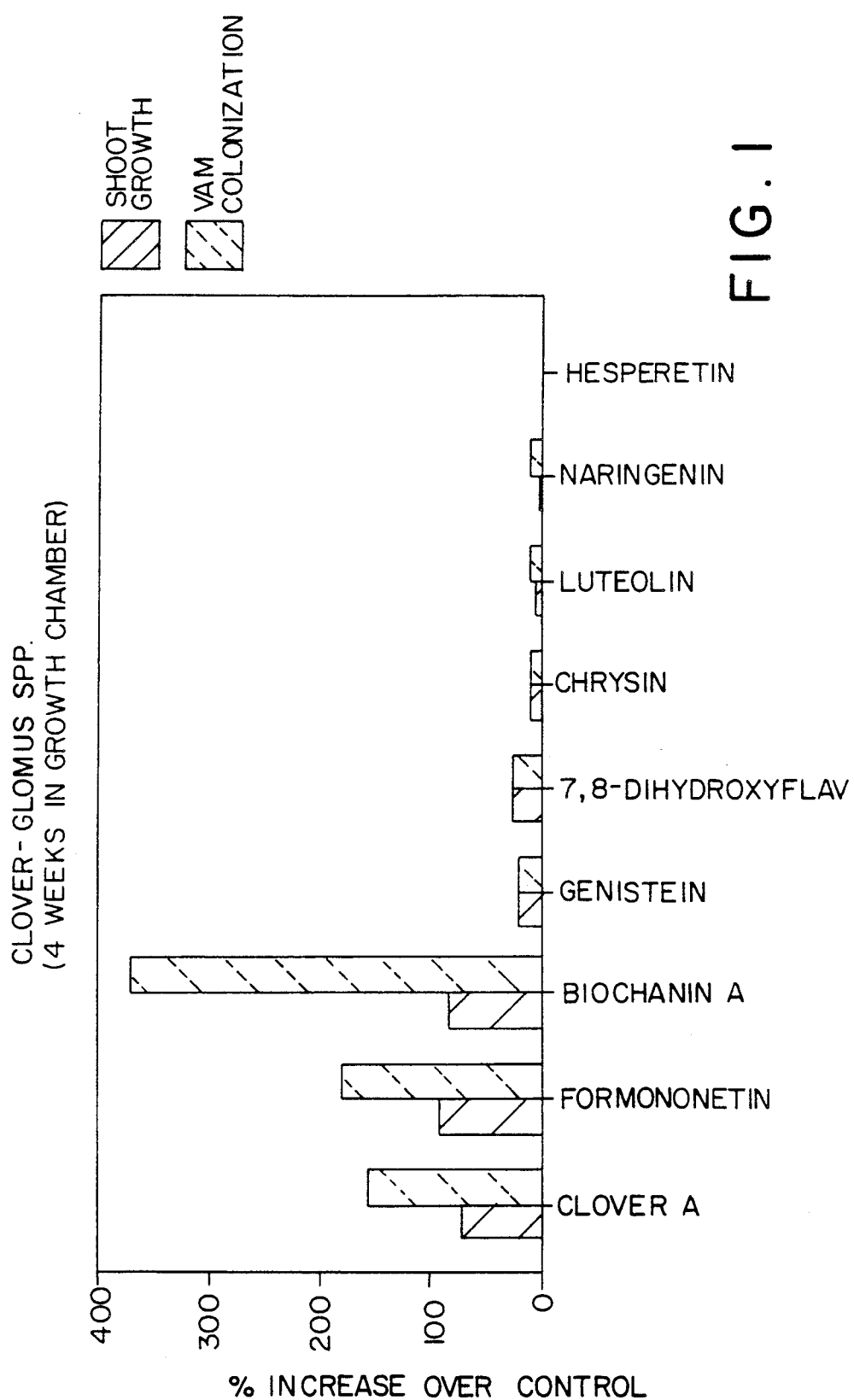
FIG. 1 shows the treatment of clover with isoflavonoids Clover A (formononetin, a natural form from the root extract); formononetin (synthetic); biochanin A compared with flavonoid compounds which are ineffective. Large increases in VAM fungus root colonization and clover growth are shown for formononetin, biochanin A and Clover A.

The present invention relates to an improvement in method for stimulating the growth of a plant material in the presence of vesicular-arbuscular mycorrhizal fungi which comprises: growing the plant material with the fungi in the presence of an isoflavonoid preferably of the formula

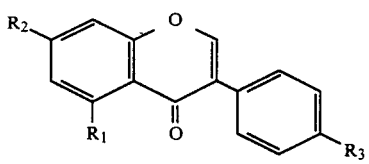

wherein $R_1$, $R_2$ and $R_3$ are selected from the group consisting of hydrogen, hydroxy and alkoxy having 1 to 30 carbon atoms.

Further the present invention relates to a plant composition useful for stimulating the growth of a plant which comprises: an isoflavonoid compound preferably of the formula

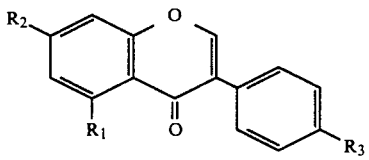

wherein $R_1$, $R_2$ and $R_3$ are selected from the group consisting of hydrogen, hydroxy and alkoxy having 1 to 30 carbon atoms; and a plant material containing the isoflavonoid compound as an additive in an amount which stimulates the growth of the plant material when the plant material is grown in the presence of VAM fungi.

Further still the present invention relates to a method for growing vesicular-arbuscular mycorrhizal fungi including spores of the fungi useful for stimulating plant growth which comprises: growing the vesicular-arbuscular mycorrhizal fungi in the presence of an amount of an isoflavonoid preferably of the formula

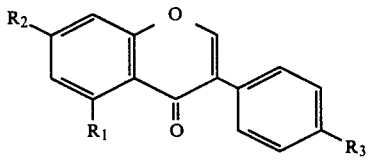

wherein $R_1$, $R_2$ and $R_3$ are selected from the group consisting of hydrogen, hydroxyl and alkoxy containing 1 to 30 carbon atoms so that the fungi produced stimulate the growth of the plant.

The present invention also relates to a fungal composition which comprises: vesicular-arbuscular mycorrhizal fungi which have been grown in the presence of an isoflavonoid preferably of the formula

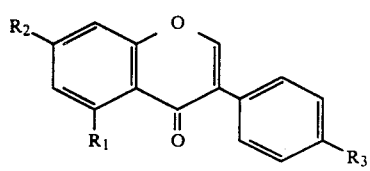

wherein $R_1$, $R_2$ and $R_3$ are selected from the group consisting of hydrogen, hydroxyl and alkoxy containing 1 to 30 carbon atoms.

Further, the present invention relates to a method for stimulating the growth of a plant in culture which comprises: growing a plant or cells of the plant in a culture solution containing vesicular-arbuscular mycorrhizal fungi and an isoflavonoid preferably of the formula:

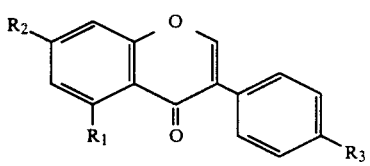

wherein $R_1$, $R_2$ and $R_3$ are selected from the group consisting of hydrogen, hydroxyl and alkoxy containing 1 to 30 carbon atoms.

Finally the present invention relates to a novel compound of the formula:

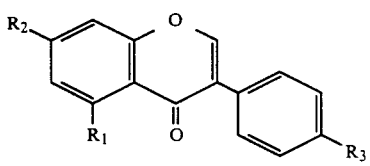

wherein $R_1$, $R_2$, and $R_3$ are selected from the group consisting of alkoxy groups containing 1 to 30 carbon atoms.

Various long chain alkoxy groups can be attached to the isoflavonoid. These groups are selected so as not to interfere with the stimulation of the VAM fungi.

The most preferred isoflavonoid compounds of the present invention are of the formula:

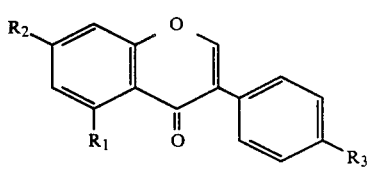

wherein $R_1$, $R_2$ and $R_3$ are as shown in Table 1.

TABLE 1

|     | $R_1$ | $R_2$ | $R_3$ |
| --- | --- | --- | --- |
| (1) | H   | H   | H   |
| (2) | OH  | OH  | OMe |
| (3) | OMe | OMe | OMe |
| (4) | H   | OH  | OMe |
| (5) | OH  | OMe | OMe |
| (6) | H   | OMe | OMe |
| (7) | H   | OMe | OH  |
| (8) | H   | H   | OMe |

Most preferred are biochanin A (2) and formononetin (4).

Isoflavonoid compounds that stimulate fungal hyphal growth in vitro were isolated from host roots and chemically identified as formononetin and biochanin A. Formononetin was later synthesized. Thus, large VAM fungi growth stimulation was found in response to formononetin and biochanin A at 5 ppm concentrations. These root factors were used as a plant growth promoting substance, either by increasing VAM formation with indigenous soil fungal populations or by stimulating formation of the external mycelium network in the soil which in turn increases the plant's capability of taking up nutrients and water from the soil.

The plant material can be rooted plants or plant tissue cells, organs, seeds or other parts of the plant and can be grown in culture with the VAM fungi. The preferred plant materials are corn, soybean, sorghum, asparagus, leek, onion, Taxus sp., coffee, clover, citrus, sea oats, wheat, potatoes and other crop plants, particularly those plants having roots which are colonized by the VAM fungi. The isoflavonoid is used in an amount between about 0.1 and 400 ppm in soil or planting mixes. Planting mixes can include vermiculite, polystyrene beads, peat moss and other fillers and growth factors. In tissue culture, the isoflavonoid is present in an amount between about 0.0001 and 400 ppm with the plant material and VAM fungi.

The isoflavonoid can be applied to the soil or planting mix either before or after the plants are planted. Preferably the isoflavonoid is applied at the time of planting of the seed. The VAM fungi can also be applied or they can be naturally present in the soil.

The isoflavonoid can be applied to the plant material, e.g. either to the seed or a propagule. Preferably the isoflavonoid is coated on the seed using an adhesive such as methyl cellulose, which is compatible with plant growth. The isoflavonoid can also be impregnated into the seed. Preferably the VAM fungi and seeds coated with the isoflavonoid are applied together The VAM fungi can also be cultured with the isoflavonoid.

The preferred VAM fungi are in the genus Glomus such as G. fasciculatum, G. intraradices and G. etunicatum.

These VAM fungi are particularly important commercially. It is preferred that the VAM fungi are grown in the presence of the isoflavonoid in an amount between about 0.0001 and 400 ppm in the culture medium. The culture medium contains sources of carbon, nitrogen, minerals and vitamins as is known to those skilled in the art.

The isoflavonoids can be applied in a liquid agricultural carrier with a dispersant which maintains the isoflavonoid in solution in an amount between about 0.1 and 400 micrograms per ml. Preferred dispersants are lower alkanols, particularly methanol, with various surfactants including anionic and cationic surfactants. Other organic solvents can be used to form emulsions of the isoflavonoid in water. The isoflavonoids can be provided in a solid mixture including the dispersant and the isoflavonoid. The composition can be formulated in solid carriers which aid in dispersing the isoflavonoid in the soil or planting material. The isoflavonoid is present in an amount between about 0.1 and 400 ppm by weight of the solid carrier.

The isoflavones can be formulated as wettable powders, flow concentrates, emulsifiable concentrates, granular formulations and the like.

Wettable powders can be prepared by grinding together about 20% to 45% by weight of a finely divided carrier such as kaolin, bentonite, diatomaceous earth, attapulgite, or the like, 45% to 80% by weight of the active compound, 2% to 5% by weight of a dispersing agent such as sodium lignosulfonate, and 2% to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 5% to 25% by weight of the active ingredient in about 65% to 90% by weight of N-methylpyrrolidone, isophorone, butyl cellosolve, methylacetate or the like and dispersing therein about 5% to 10% by weight of a nonionic surfactant such as an alkylphenoxy polyethoxy alcohol. This concentrate is dispersed in water for application as a liquid spray.

When the isoflavonoids are used for soil treatment, the compounds may be prepared and applied as granular products. Preparation of the granular product can be achieved by dissolving the active compound in a solvent such as methylene chloride, N-methylpyrrolidone or the like and spraying the thus prepared solution on a granular carrier such as corncob grits, sand, attapulgite, kaolin or the like.

The granular product thus prepared generally comprises about 3% to 20% by weight of the active ingredient and about 97% to 80% by weight of the granular carrier.

The isoflavonoids can also be mixed with a herbicide or pesticide which is applied to the plants or applied before or after the application of the herbicide or pesticide. The VAM fungi function as a "safener" in the presence of the isoflavonoids, and overcome injury caused by the herbicides or pesticides. Injury caused by imidazolinone herbicides, such as imazaquin and imazethapyr, and pendimethalin are particularly overcome by the method of the present invention. Best results are seen when the composition is applied the year following a herbicide application to fields showing residual levels of herbicide sufficient to cause injury to crops planted into the field.

The novel compound of the formula

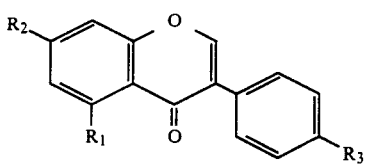

wherein $R_1$, $R_2$ and $R_3$ are selected from the group consisting of alkoxy groups containing 1 to 30 carbon atoms has increased water solubility over the known hydroxy substituted isoflavonoids. In the preparation of the novel compounds a hydroxy flavonoid such as (2) in Table 1 is alkylated by reaction with an alkyl halide (chloride, bromide or iodide) in the presence of a base or acid and organic solvents such as dichloromethane acetone, and the like. The mixture is refluxed for several hours, preferably 12 to 24 hours. Essentially the reaction is a conventional alkylation reaction of phenols.

The isoflavonoids in Table 1 are available commercially except for the peralkoxy isoflavonoids. They have been prepared by alkylation of the isoflavonoids in Table 1.

SPECIFIC DESCRIPTION
EXAMPLE 1

The isoflavonoids were initially isolated from clover roots and then were identified as formononetin and biochanin A. The isoflavonoids were isolated from clover roots by the general scheme shown in Table 2. FIGS. 3 to 6 show the spectral data for natural and synthetic formononetin.

TABLE 2

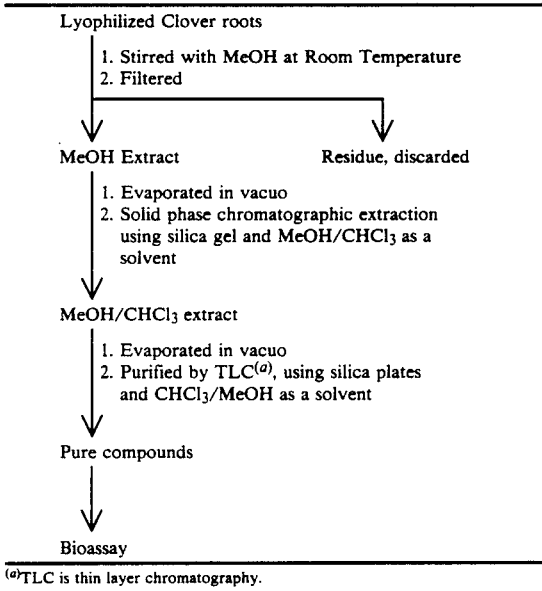

Lyophilized Clover roots
1. Stirred with MeOH at Room Temperature
2. Filtered

MeOH Extract          Residue, discarded

1. Evaporated in vacuo
2. Solid phase chromatographic extraction using silica gel and MeOH/CHCl$_3$ as a solvent MeOH/CHCl$_3$ extract 1. Evaporated in vacuo
2. Purified by TLC$^{(a)}$, using silica plates and CHCl$_3$/MeOH as a solvent Pure compounds Bioassay $^{(a)}$TLC is thin layer chromatography.

Two active compounds from TLC were chemically characterized. The high Rf compound, clover A, was found to be identical to formononetin, 7-hydroxy, 4'-methoxy isoflavone. This was confirmed by $^1$H, $^{13}$C-NMR, long range COSY and a direct comparison with synthetic Formononetin as in FIGS. 3 to 6.

The lower Rf compound was eluted with CHCl$_3$/MeOH and afforded a pale brown solid, H-NMR (CDCl$_3$/DMSO) δ 8.00 (1H, s, H-2), 7.40 (2H, d, J=8Hz, H-2', H-6'), 6.90 (2H, d, J=8Hz, H-3', H-5'), 6.35 (1H, d, J=1.8Hz, H-8), 6.25 (1H, d, J=1.8Hz, H-6), 3.75 (3H, s, OMe); Molecular ion at m/z 284. Comparison of these data to the reported values of biochanin A confirmed that the low Rf compound isolated from clover root is also biochanin A.

The two compounds chemically identified were 7-hydroxy,4'-methoxy isoflavone (Table 1, 4) (formononetin) and 5,7-dihydroxy,4'-methoxy isoflavone (Table 1, 2) (biochanin A). These compounds were active in the 0.1 to 400 ppm concentration range and are unknown for this use.

Initially, root exudates from Ladino white clover seedlings were obtained from plants at 2 weeks of age that had been grown in a nutrient solution with no phosphorus as shown in Table 3.

TABLE 3

| Composition of nutrient solution | |
|---|---|
| Components | Concentration, mg/l |
| KNO$_3$ | 606.60 |
| Ca(NO$_3$)$_2$.4H$_2$O | 656.40 |
| MgSO$_4$.7H$_2$O | 240.80 |
| H$_3$BO$_3$ | 2.86 |
| MnCl$_2$.4H$_2$O | 1.81 |
| ZnSO$_4$.7H$_2$O | 0.22 |
| CuSO$_4$.5H$_2$O | 0.08 |
| H$_2$MoO$_4$ | 0.02 |
| Fe-tartrate | 5.00 |

Adjust to pH 6.8 with 0.1N NaOH

The root exudates of these seedlings were lyophilized and extracted with MeOH at room temperature. The MeOH extract was dried in vacuo and the resultant crude extract was chromatographed on silica gel thin layer plates using a 4:1 chloroform-methanol solvent system. Three bands, detected under long and short wavelength UV light (254 and 366 nm), were eluted separately using 1:1 MeOH—CHCl$_3$ and evaporated to dryness. These pure fractions were bioassayed for their ability to stimulate VAM hyphal growth on agar media and found to be active in this capacity. Since the exudate fraction had low concentrations of active compound, clover roots were extracted in order to obtain these compounds. The clover roots were obtained from plants less than 2 weeks of age that had been grown in unsterilized sand and watered with distilled water daily. The roots were lyophilized at 5° C. and extracted with MeOH at room temperature. The MeOH solvent was removed under vacuum at 40° C. and the resultant extract was partially purified by solid phase extraction on silica gel using MeOH under vacuum, evaporated to dryness using a rotary evaporator and the resultant product purified on tapered thin layer plates (silica, 4:1 chloroform-methanol). Three bands with identical Rf values to the root exudate were collected, extracted, and processed as before. The pure compounds obtained were identical to the compounds from the root exudate in VAM biological activity. Two compounds were chosen, the highest and middle Rf value compounds, for immediate identification and for VAM fungal growth studies. These compounds were characterized by $^1$H- and $^{13}$C-NMR and MS methods and found to be isoflavones with one methoxy substituent attached to ring B and hydroxy group(s) on ring A as follows:

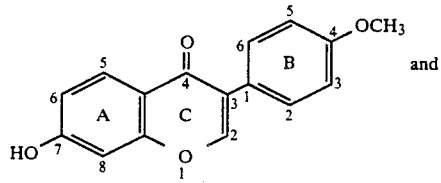

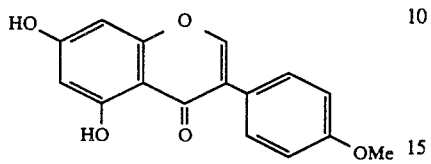

H-NMR spectral analysis showed the active compound to be identical to 7-hydroxy-4'-methoxyisoflavone (formononetin compound 4 Table 1) and 5,7-dihydroxy-4'-methoxy isoflavone, (Biochanin A, Compound 2, Table 1).

(1) Crude Production of Isoflavonoids

White clover (Trifolium repens cv. Ladino) seeds and seeds from other plant types were surface sterilized with 70% ethyl alcohol for 30 seconds followed by 0.1% $HgCl_2$ in 1 mM HCl for 5-7 minutes followed by exhaustive washing with sterile distilled water.

The seeds were then placed on moist filter paper in a sterile petri dish incubated at 23° C. in the dark for 2 days to allow germination. Fifty seedlings were transferred from the petri dish to moist cheese cloth in a sterilized glass dish containing 100 ml of sterilized Hoagland's nutrient solution, without phosphorus. The dishes were enclosed in sterile clear plastic bags, tightly sealed and the seedlings grown under 16 hour day length fluorescent lights (4.5 lux). The Hoagland's solution was replaced at weekly intervals.

At weekly intervals, exudates or extracts were collected from the roots of these clover and other seedlings. Weekly, solutions are pooled, filter sterilized, rotary evaporated to 1/10 original volume, filter sterilized again, lyophilized, and stored at 4° C.

(2) Chemical Characterization

The chemical characterization of active fractions containing the isoflavonoids from various plant sources was according to established procedures. At each stage of purification or characterization, portions of extract were produced for determination of VAM fungal growth stimulating activity. The results of the bioassay enabled further chemical characterization of the isoflavonoids.

EXAMPLE 2

Based on the chemistry of the compounds formononetin and biochanin A isolated from clover roots, the VAM biological activity of additional commercially available flavonoids were investigated along with formononetin and biochanin A and the experiments were conducted to determine if other compounds would stimulate VAM fungal root colonization and subsequent plant growth. Clover plants were used and grown in a substrate infested with either Glomus intraradices or a fungus resembling Glomus fasciculatum.

Disinfected pre-germinated clover seeds were transplanted into a sand soil mix (2:1) in plastic inserts containing four 60 cc individual cells. Each four-cell unit was placed in 90 × 15 mm plastic petri dish bottom to avoid chemical contamination and to facilitate watering. Free VAM propagule sand soil mix was infested with a VAM fungal soil inoculum of either a Glomus fasciculatum-like fungus or Glomus intraradices. The substrate had a neutral pH, low exchange capacity, and a low to moderate fertility level. The VAM soil inoculum was obtained from pot culture kept in the greenhouse for at least 4 months. Dried inoculum was mixed thoroughly with the substrate in order to achieve a final spore density ranging from 2 to 5 spores per gram of the soil mix.

Before transplanting the seeds, between 5 to 10 ml of 5 ppm solutions of either Clover A (isolated natural form of formononetin) or other pure chemicals were delivered per each cell. The inserts were placed in plastic trays and transferred to a full light growth chamber set at 14 hours of light per day plus 10 hours of dark per day length.

The plants were watered twice a day with distilled water and allowed to grow for 4 weeks, after which they were harvested. Growth responses were measured as shoot fresh weight. Roots were separated from the soil and used for VAM root colonization assessments.

Figure 7:
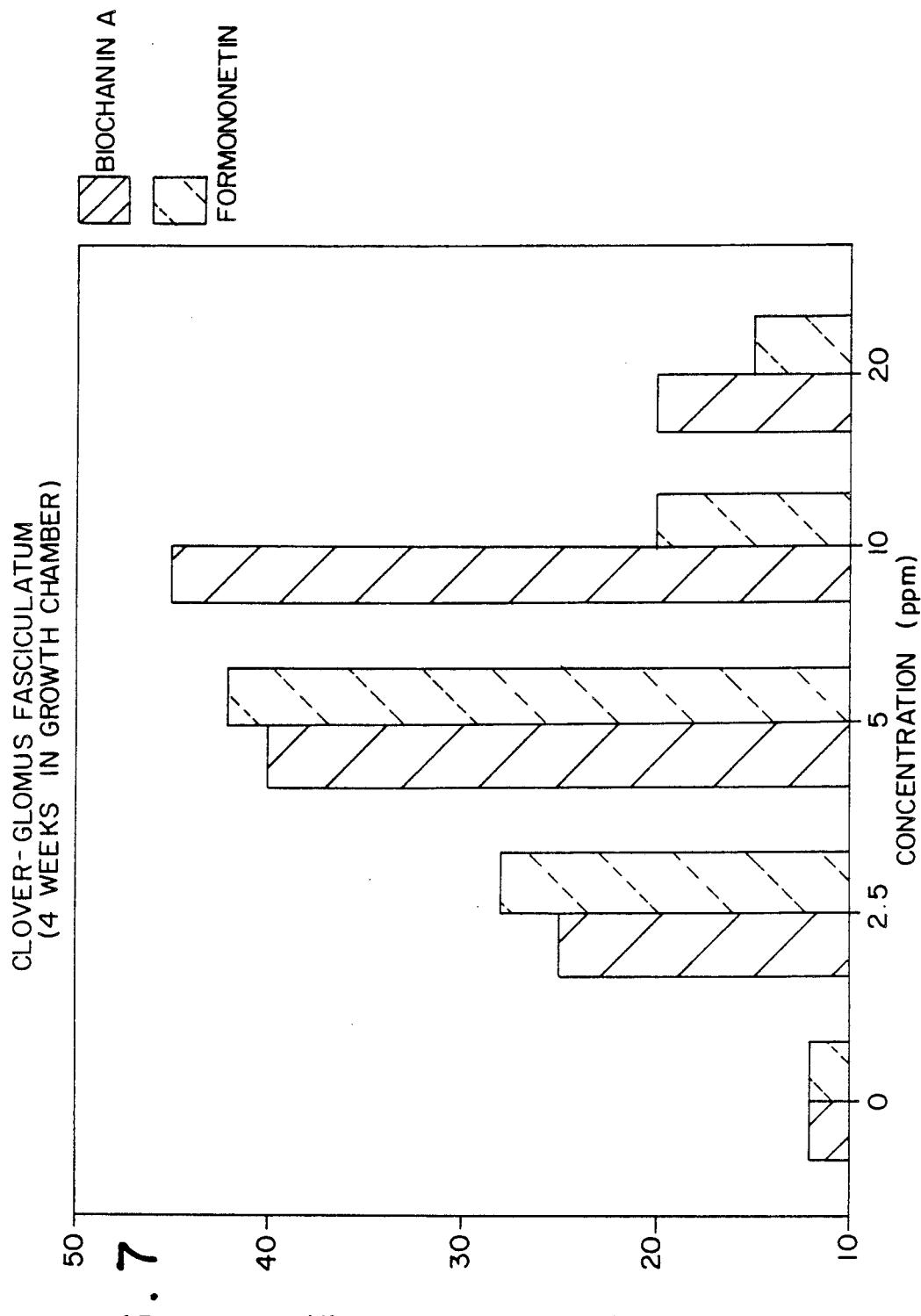
FIG. 7 shows the percent VAM fungus root colonization as a function of concentration of biochanin A and formononetin.

As shown in FIG. 1, the isoflavonoids formononetin (both the natural and synthesized form) and biochanin A stimulated VAM fungal root colonization as well as clover plant growth when the plants were allowed to grow in a VAM fungus infested substrate. The other ineffective compounds tested, genestein, 7-8 dihydroxyflavone, chrysin, luteolin, naringenin and hesepertin failed to improve plant growth or VAM fungus root colonization. FIG. 7 shows the affect of concentration of biochanin A and formononetin on percent VAM fungus colonization for clover. Similar increases in growth and fungal root colonization have been observed for corn and sorghum after treatment with formononetin and biochanin A.

EXAMPLE 3

FIGS. 8 and 10 show the growth and FIG. 9 shows the herbicide injury level of corn seedlings grown in an unsterilized field soil in the presence or absence of formononetin (Form), biochanin A (Bio) or the VAM fungus Glomus intraradices (Myc) at an added rate of 7 spores/gram soil. The field soil contained an initial residual level of 13 ppb of the herbicide imazaquin and an indigenous VAM fungus level of approximately 7 spores/gram soil. Leaf area measurements of the third leaf from the soil were taken at 2 and 3 weeks after the pre-germinated corn seeds were transplanted and grown in the field soil in 3 ¼"×6" Styrofoam pots in a growth chamber. The growth chamber had a day temperature of 30° C. and a night temperature of 25° C. and 14 hours of light per day plus 10 hours of dark per day. FIG. 8 shows the increased areas of corn leaves at 2 and 3 weeks after treatment with formononetin (-Myc-Form), biochanin A (-MycBio), or the VAM fungus Glomus intraradices in comparison to the control plants (-myc control). Adding biochanin A or formononetin along with the added VAM fungus inoculum (+MycBio or +MycForm) also increased corn leaf areas.

FIG. 9 shows the herbicide injury of the corn seedlings described in FIG. 8 (above) at 2 and 3 weeks after transplanting. The injury rating scale based on the intensity of leaf chlorosis ranged from 0=no injury to 5=severe. Both formononetin and biochanin A reduced the herbicide injury of the corn plants in comparison to plants not receiving these compounds.

FIG. 10 shows the percent increase in dry weight of tops of the corn plants described in FIG. 8 in comparison to non VAM inoculated control at four weeks of age. Treatment with formononetin or biochanin A increased the dry weight of tops of the corn plants.

EXAMPLE 4

1. Spore Production

VAM spores of several fungal species were obtained by growing sorghum plants in pots with disinfected soil in the presence of spores to be multiplied. These spores germinate and infect the growing plants with the resulting mycorrhizal infections producing new spore in the soil in 3 to 4 months. The resulting spores were used for experimental purposes. After sporulation, pot cultures were stored at 4° C. for at least 30 days before use. This VAM infested soil was wet sieved to eliminate most of the soil and organic debris which was collected on the sieve. Next a modified centrifugation-flotation technique in Ficoll solutions of various densities was used to isolate spores from the soil debris. Organic debris was further removed from the spore suspension by hand with a Pasteur pipet under a dissecting microscope. Spores were then surface-sterilized with a solution containing 2% Chloramine-T (w/v), +200 ppm of Streptomycin, before use for germination and hyphal growth studies.

2. Germination and Hyphal Growth Bioassay

Figure 2:
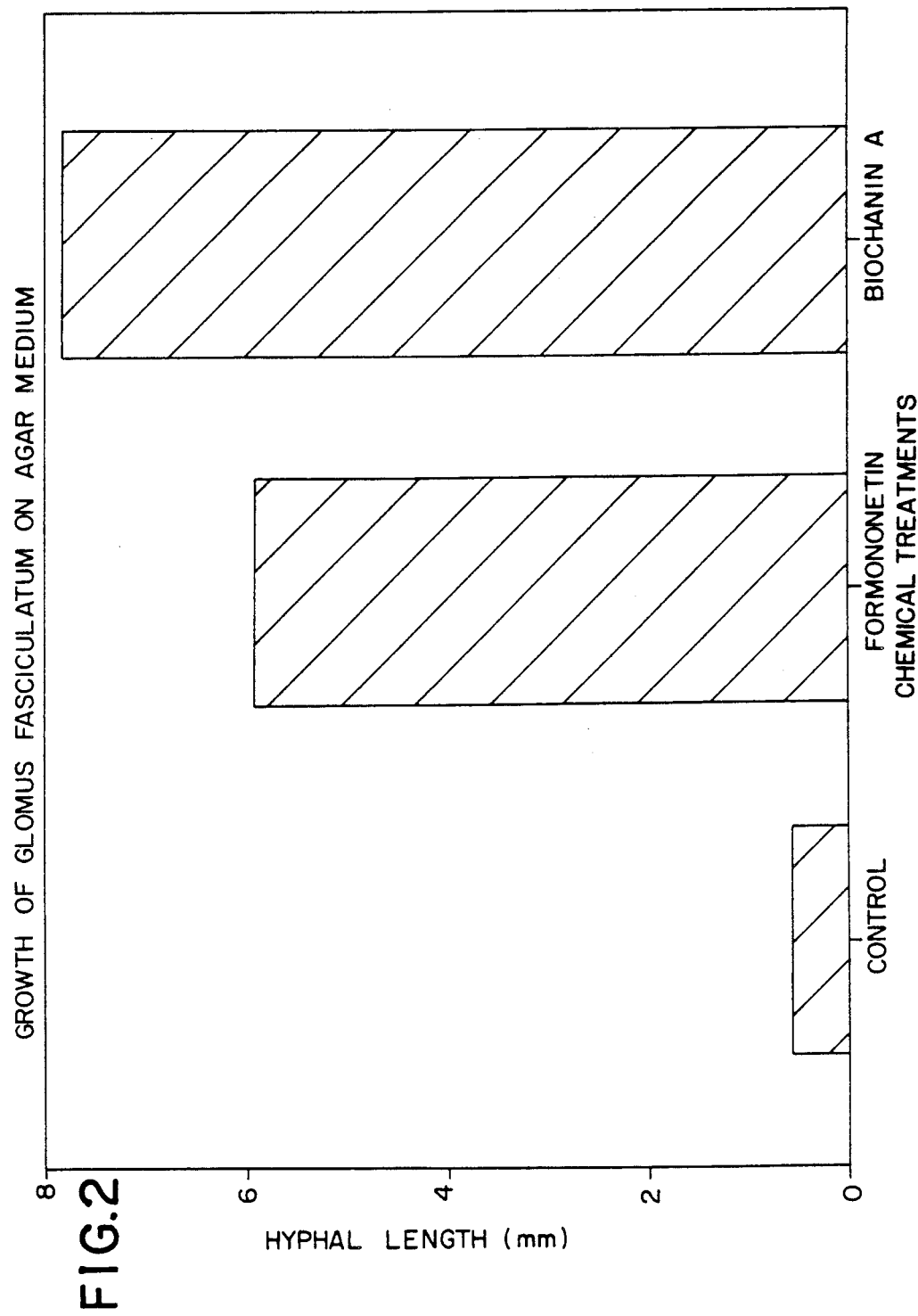
FIG. 2 shows the growth of a VAM fungus having the characteristics of Glomus fasciculatum on nutrient media containing biochanin A; formononetin; and a control lacking either of these two chemicals. Large increases in fungus growth are caused by addition of formononetin or biochanin A in relation to the control.
Figure 3:
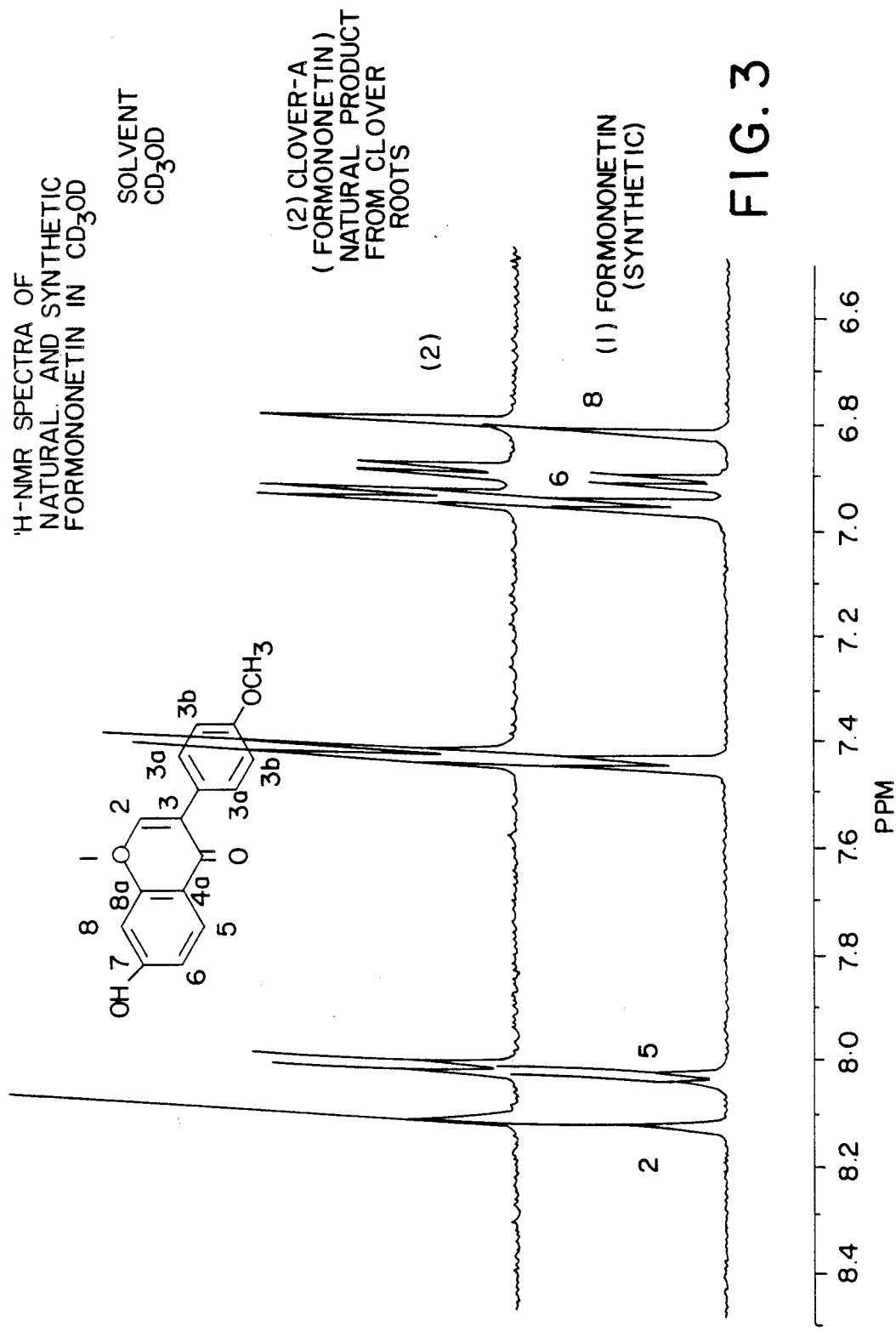
FIGS. 3 to 6 show the spectral data for natural and synthetic formononetin in $CD_3OD$ and DMSO.
Figure 4:
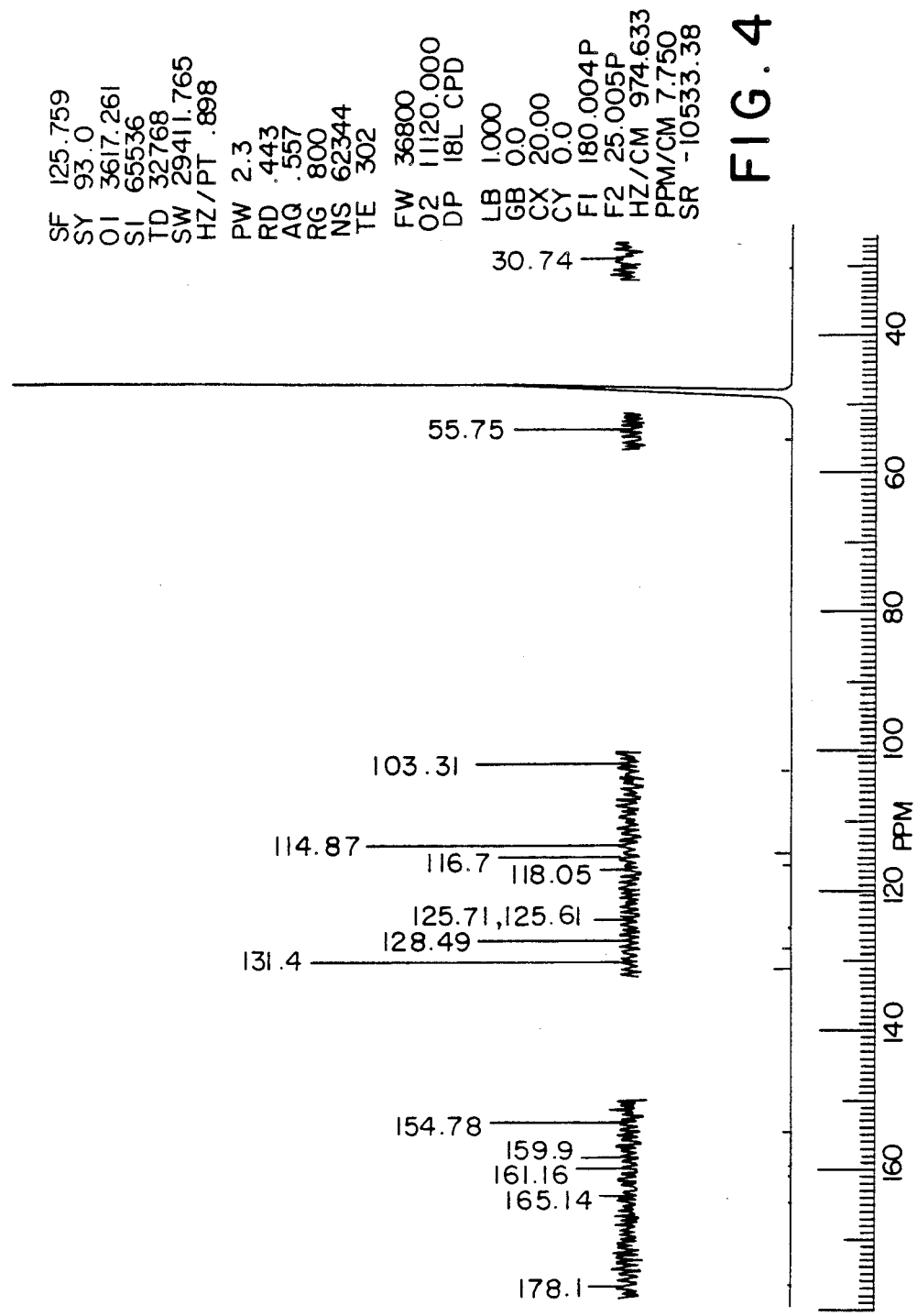
Figure 5:
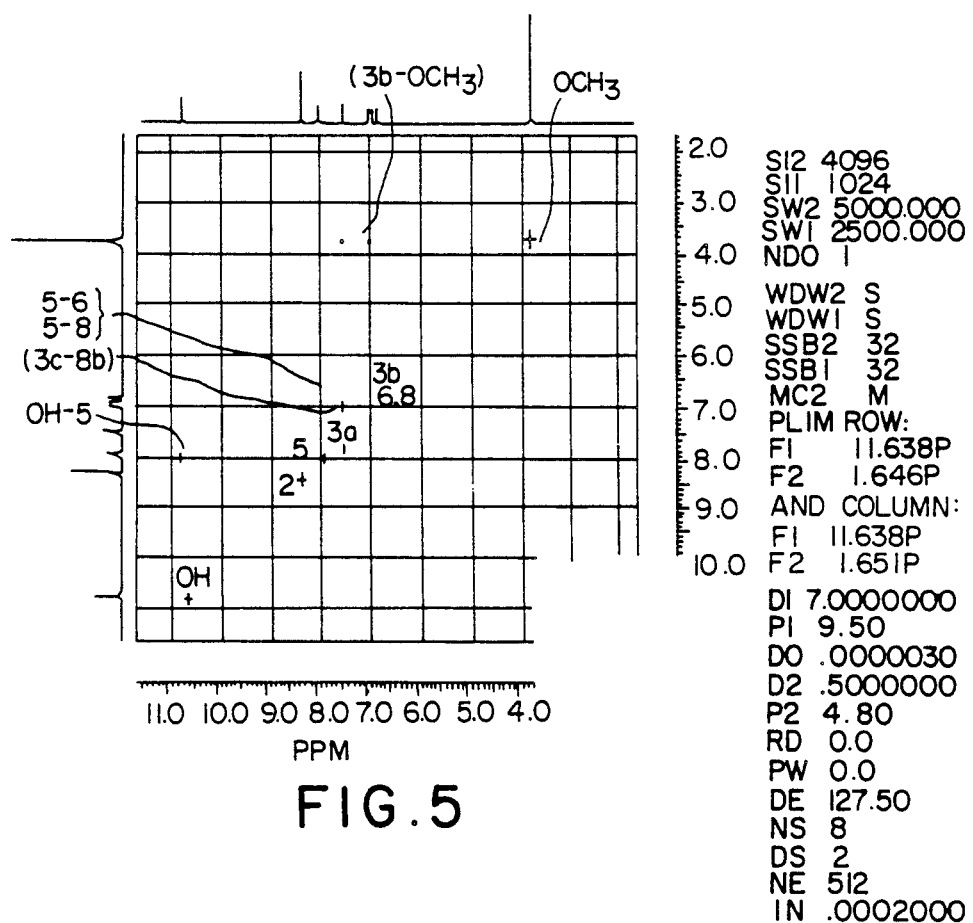
Figure 6:
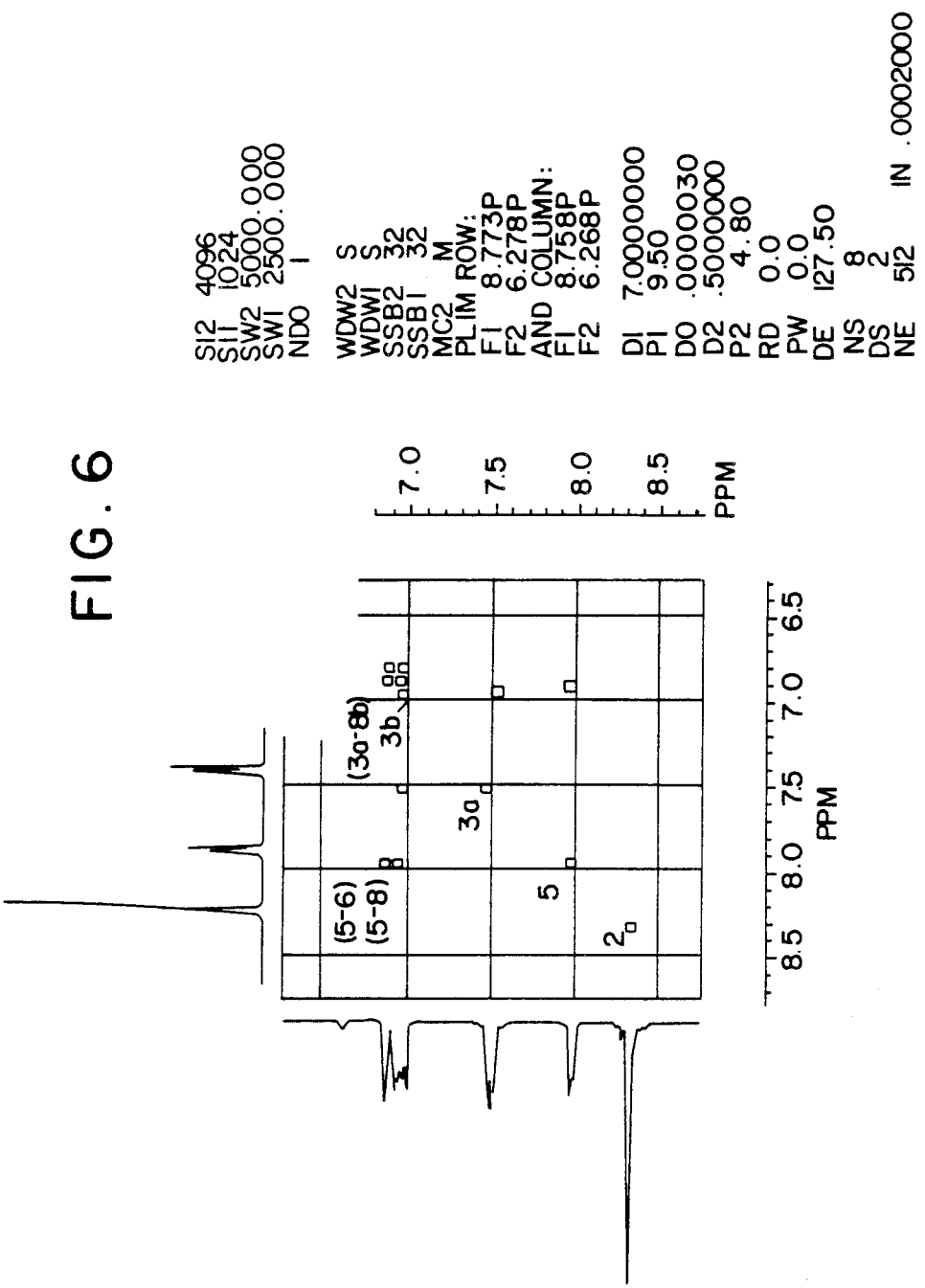

Formononetin and biochanin A were added to agar at a range of concentrations per volume of media. Germination and hyphal elongation of the VAM spores was monitored. Germination was defined as a germ tube that was at least twice the diameter of the spore. Hyphal elongation effects were the mean hyphal length of only those spores that germinate. The bioassay time was shortened to 2 weeks from 4 weeks. There were two additional methods for bioassaying fungal growth. The first method used liquid culture, and the second involved a membrane sandwich containing VAM spores superimposed over sterile sand containing nutrients. Both of these procedures produced similar results in 1 week. The results from agar media are shown in FIG. 2 for a VAM fungus resembling *Glomus fasciculatum*.

EXAMPLE 5

Methylation

Formononetin (250 mg) and biochanin A (500 mg) were separately dissolved in acetone (25 ml) and stirred with anhydrous $K_2CO_3$ (30 g), (5 min) at room temperature. Dimethyl sulphate (3 ml each) was added to the above reaction mixture and refluxed for 18 hours. Reaction mixture was cooled, filtered separately and rotary evaporated with methanol. The crude products were crystallized from methanol and dried under vacuum. Melting points were taken for the methylated product on a Kofler hot stage apparatus and were uncorrected. The physical properties of the permethoxy isoflavonoids are as follows:

MP, 7-methoxy, 4'methyl isoflavone=155–1.56° C. (white, plate-like crystals), Molecular weight 282.

MP, 5,7-dimethoxy, 4'methoxy isoflavone=158–160° C. (pale yellow, plate-like crystals), Molecular weight 312.

Solubility: 5,7-dimethoxy, 4'methoxy isoflavone and 7-methoxy, 4'methyl isoflavone=soluble in methanol, methanol-water, partially soluble in $CHCl_3$.

The increased water solubility of these isoflavonoids makes them particularly useful.

EXAMPLE 6

The method of Example 4 can be used to methylate other hydroxy containing isoflavonoids shown in Table 2, such as formononetin. This process produces known compounds.

It is intended that the foregoing description be only illustrative of the present invention and that the present invention be limited only by the hereinafter appended claims.

We claim:

1. In a method for stimulating the growth of a plant material in the presence of vesicular-arbuscular mycorrhizal fungi, the improvement which comprises:
    growing the plant material with the fungi in the presence of an isoflavonoid.

2. In a method for stimulating the growth of a plant material in the presence of vesicular-arbuscular mycorrhizal fungi, the improvement which comprises:
    growing the plant material with the fungi in the presence of an isoflavonoid of the formula

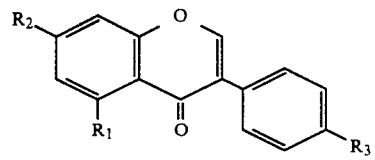

wherein $R_1$, $R_2$ and $R_3$ are selected from the group consisting of hydrogen, hydroxy and alkoxy having 1 to 30 carbon atoms.

3. In a method for stimulating the growth of a plant material in the presence of vesicular-arbuscular mycorrhizal fungi, the improvement which comprises:
    growing the plant material with the fungi in the presence of an amount of an isoflavonoid compound selected from the group consisting of formononetin and biochanin A and mixtures thereof which stimulates the growth of the plant material.

4. A method for stimulating the growth of a plant planted in soil or planting mixes containing vesicular-arbuscular mycorrhizal fungi which comprises:
    applying an amount of an isoflavonoid compound selected from the group consisting of formononetin and biochanin A and mixtures thereof to the soil so as to stimulate the growth of the plant.

5. The method of claim 4 wherein the amount of the isoflavonoid is applied in an amount between about 0.1 and 400 ppm in the soil or planting mixes.

6. The method of claim 5 wherein the fungi are applied with the isoflavonoid.

7. The method of claim 4 wherein the plant is selected from the group consisting of plants having roots colonized by these fungi.

8. The method of claim 4 wherein a seed or a propagule is planted and the isoflavonoid is applied at about the time of planting.

9. The method of claim 8 wherein the seed or a propagule is coated with the isoflavonoid.

10. A method for stimulating the growth of a plant in culture which comprises:

(a) providing a plant or cells of the plant in a culture solution containing vesicular-arbuscular mycorrhizal fungi and a compound selected from the group consisting of formononetin and biochanin A and mixtures thereof; and (b) growing the plant in the culture solution.

11. The method of claim 10 wherein the plant is colonized by the fungi.

12. The method of claim 10 wherein the amount of the flavonoid is between about 0.1 and 400 ppm in the solution.

* * * * *